United States Patent
Bühren et al.

(10) Patent No.: US 9,351,634 B2
(45) Date of Patent: May 31, 2016

(54) METHOD FOR AUTOMATIC OPTIMIZATION OF THE CALCULATION OF AN INTRAOCULAR LENS TO BE IMPLANTED

(75) Inventors: Tobias Bühren, Magdala (DE); Michael Trost, Stadtroda (DE); Burkhard Wagner, Jena (DE)

(73) Assignee: Carl Zeiss Meditec AG, Jena (DE)

( * ) Notice: Subject to any disclaimer, the term of this patent is extended or adjusted under 35 U.S.C. 154(b) by 69 days.

(21) Appl. No.: 14/344,572

(22) PCT Filed: Sep. 14, 2012

(86) PCT No.: PCT/EP2012/068077
§ 371 (c)(1),
(2), (4) Date: Mar. 12, 2014

(87) PCT Pub. No.: WO2013/037946
PCT Pub. Date: Mar. 21, 2013

(65) Prior Publication Data
US 2014/0327884 A1 Nov. 6, 2014

(30) Foreign Application Priority Data
Sep. 16, 2011 (DE) .......................... 10 2011 113 953

(51) Int. Cl.
*A61B 3/00* (2006.01)
*A61F 2/16* (2006.01)
(52) U.S. Cl.
CPC .................. *A61B 3/0025* (2013.01); *A61F 2/16* (2013.01); *A61F 2002/1697* (2013.01); *A61F 2002/1699* (2015.04)

(58) Field of Classification Search
USPC ......................................................... 359/246
See application file for complete search history.

(56) References Cited

FOREIGN PATENT DOCUMENTS

WO WO 2010/028654 A1 3/2010

OTHER PUBLICATIONS

PCT International Preliminary Report on Patentability (Form PCT/IB/338, Form PCT/IB/2373), PCT Written Opinion of the International Searching Authority (PCT/ISA/237) for PCT/EP2012/068077 (10 total pages).
Preussner, P.-R. et al; "Intraocular lens calculation accuracy limits in normal eyes," J Cataract Refract Surg—vol. 34, May 2008; 802-808.
Preussner, P.-R. et al; "Ray tracing for intraocular lens calculation," J Cataract Refract Surg—vol. 28, Aug. 2002; 1-10.

*Primary Examiner* — Jack Dinh
(74) *Attorney, Agent, or Firm* — Patterson Thuente Pedersen, P.A.

(57) ABSTRACT

A method for calculating the values of an intraocular lens to be implanted, wherein the results of numerous cataract operations are taken into account in the calculation for intraocular lenses to be implanted in the future. At least the corneal topography, the length of the eye and the depth of the anterior chamber are determined pre-operatively, the values of the IOL to be implanted are calculated by means of ray-tracing, and at least the corneal topography, the length of the eye, the depth of the anterior chamber and the objective, wavefront-based residual refraction are determined post-operatively. The measurement values determined pre-operatively and post-operatively are used to optimize the surgically-induced astigmatism and the post-operative anatomical lens position for calculating the values of IOLs to be implanted in the future.

9 Claims, No Drawings

METHOD FOR AUTOMATIC OPTIMIZATION OF THE CALCULATION OF AN INTRAOCULAR LENS TO BE IMPLANTED

RELATED APPLICATIONS

The present application is a National Phase entry of PCT Application No. PCT/EP2012/068077, filed Sep. 14, 2012, which claims priority from DE Application No. 10 2011 113 953.6 filed Sep. 16, 2011, which applications are hereby incorporated by reference herein in their entirety.

BACKGROUND

The present invention relates to an improved method for calculating an intraocular lens to be implanted, with which method the calculation is automatically optimized in that the results of numerous cataract surgeries are taken into account during the calculation for intraocular lenses (IOL) to be implanted in the future.

According to the known prior art, IOLs are selected or adapted based on measured and/or estimated variables, only individual parameters in the form of individual measured values or as a mean for a defined patient group being taken into account.

The optimal intraocular lens (IOL) is selected or adapted exclusively according to its features, such as for instance type, refractive power, asphericity, and multifocality. No consideration is given to potential interrelationships with specific contributing factors to the treatment, such as patient features, diagnostics, surgical procedures, or the like, or to using statistical distribution for the parameters.

SUMMARY OF THE INVENTION

Cataract surgeons are required to select suitable intraocular lenses (IOL) for a patient. The surgeon must account for many factors. Firstly, the suitable calculation method for the IOL optical power must be selected as a function of the individual biometric parameters of the eye. For this, as a rule different more or less suitable formulas are used for the calculation for unusually long, normal, or unusually short eyes. In the simplest cases, the input parameters for these calculations are based on the keratometry and axial length of the eye. Due to their simplified model assumptions, the formulas generally also include an empirically determined correction factor, such as for instance the so-called A constant.

The currently most widely used calculation methods are so-called IOL formulas, e.g. Haigis, Holladay, Hoffer, Olsen, Shammas, and SRK IOL formulas. According to these, the refraction D (starting/evaluation parameter) of the patient after IOL insertion is calculated with:

$$D = D_{IOL} - f(K, AL, ACD, A) \quad (1)$$

where $f(\,)$ is a classically known IOL formula,
$D_{IOL}$ is the refractive power of the IOL,
K is the measured keratometry value,
AL is the measured axial length of the eye,
ACD is the measured anterior chamber depth, and
A is an IOL type-dependent constant input variable.

As a rule, the different calculation methods (biometry formulas) use different constants that are a function of the IOL type (i.e. IOL constants). An A constant is used e.g. in the SRK formula.

For selecting the IOL, the doctor provides a target refraction ($D = D_{TARGET}$). For optimization, the doctor calculates the refraction in accordance with (1) for different IOLs by varying $D_{IOL}$ and A. In many cases the doctor uses IOLs of the same type so that there is no variation in A and the optimization amounts to a formula calculation according to $D_{IOL} = D_{TARGET} + f(K, AL, ACD, A)$. Thus, if the target is emmetropia, the classic formula calculation for the IOL that results is $D_{IOL} = f(K, AL, ACD, A)$.

The constant A in the formulas is determined empirically using a patient ensemble in order to adapt the formula values to the actually resulting optimal refraction values. However, this adaptation only ensures that the mean of the refraction values for the test ensemble agrees with the formula.

The doctor typically accounts for statistical errors in the biometry formula in that he knows from experience that his actually attained refraction values for his patients will have a certain fluctuation around the target refraction. If he wants to minimize its effect, he provides a correction to the target refraction. For instance, if the doctor typically has deviations of +/−0.25 D for target refraction in patients with myopic eyes, then he will target refraction of −0.25 D in order to have a high probability of preventing the eye of the patient from being intolerably hyperopic. This method represents a good strategy for the average in the patient ensemble. However, the typical fluctuation around the target refraction or the allowance could be reduced if, instead of a mean value for a patient ensemble, individual input parameters for the individual patient were to be used as the initial variables.

Currently various approaches are used according to the prior art to minimize systematic errors. Thus, a number of doctors use a different A constant for each ethnic group among their patients. This permits a reduction in the systematic errors and also permits a reduction in statistical errors if the statistical variance in each group is lower.

Depending on defined starting conditions such as for instance patients having long axial eye lengths or that have had previous refractive corneal surgery, other doctors use different biometric formulas that are better adapted to the conditions in a specific case or that require measurement of additional parameters, such as the anterior chamber depth or lens thickness. In this case, as well, in particular the systematic errors are reduced, but statistical errors may increase due in part to the additional measured parameters.

It is a drawback of this method that the correction cannot be made on an individual basis but may only be made in the statistical mean.

It is a further drawback that in the correction only the target refraction is taken into account, but not the individual error sources that have led to the deviating target refraction. In addition, the value of the subjective refraction is necessary for the optimization process, and this value itself represents an essential error source in the determination. Finally, the process must be conducted manually, i.e. after manual determination of the post-operative target refraction, the values are assigned to the patient data and these are then manually selected in order to perform an optimization calculation.

Another problem is the optimizing method for the formulas. Improving the post-operative refraction results using the constants method takes into account all of the errors that occur during cataract surgery. These are errors during the measurement processes, errors during the IOL calculation, and unexpected events during the implantation and healing processes. However, optimizing the results exclusively using the post-surgical refraction precludes taking individual errors sources into account.

An alternative method, albeit a method that is not widely used, is ray tracing. As the term indicates ray tracing shall be construed as a method for tracing/following rays. As is known, we only perceive objects in our environment because they are irradiated by a light source and they reflect these rays of light, some of which ultimately reach our eyes. The ray tracing method simulates this elementary natural phenomenon. If the optical system, i.e., the individual human eye with all of its optical elements, is known, a "real" image occurring on the retina may be calculated by means of ray tracing. The method is thus based on a detailed eye model using the corneal topography of the eye. In this method, no general correction factors (A constants) are used, but certain assumptions regarding the effective (post-operative) lens position (ELP) must be made. This method is suitable for eyes having widely varying biometric parameters, such as for instance long eyes, normal eyes, short eyes, post-LASIK eyes, etc.

The IOL optical power and the residual refraction are then calculated using ray tracing. Various selection criteria and metrics for the calculation may be used in order to attain a good correlation to subjective visual acuity, i.e. a result comparable to what the patient experiences. Although retinal image metrics have proved to be particularly suitable, the following other selection criteria are also possible:

Evaluation of the image on the retina with respect to moment, entropy, compactness, shape, and intensity distribution by means of point spread function (PSF), line spread function (LSF), and root mean square;

Evaluation of resolution using optical transfer function (OTF), such as modulation transfer function (MTF) or phase transfer function (PTF);

Evaluation of contrast using the contrast sensitivity function (CSF);

Evaluation of optical aberrations, such as chromatic aberration, ray aberration, wave front aberration, depth of field and binocular deviation of the image scale;

Evaluation of the classic refraction parameters: diopter and astigmatism.

This list merely provide examples, because in principle other optical evaluation parameters known to one skilled in the art may also be used. In addition, in principle any evaluation parameters or criteria with which deviations from the ideal wave front may be assessed and quantified may be used.

While P.-R. Preussner et al compare the use of ray tracing methods and IOL formulas in [1], in [2] they go into more detail regarding a calculation model that is based on a method of ray tracing. In this case, based on the individual measured values and estimated variables such as especially the position of the IOL in the eye, an eye model with as a rule a plurality of optically active surfaces is developed and is calculated for one or a plurality of rays using methods from the optical design. The image quality on the retina/fovea is calculated as the evaluation value. With appropriately precise determination of the input variables this makes it possible to avoid systematic errors to a large extent. Statistical errors that result for example from lack of reproducibility of measurements or from fluctuations in the wound healing process are not taken into account here, either.

Literature

[1] Preussner, P.-R. et al; "Intraocular lens calculation accuracy limits in normal eyes," J CATARACT REFRACT SURG—VOL 34, May 2008;
[2] Preussner, P.-R. et al; "Ray tracing for intraocular lens calculation," J CATARACT REFRACT SURG—VOL 28, August 2002;

The underlying object of the present invention to improve the method for calculating an intraocular lens to be implanted such that results from numerous cataract operations are taken into account in the calculation of intraocular lenses (IOL) to be implanted and the calculation is automatically optimized because of this.

In accordance with the invention, the object is attained using the features in the independent claims. Preferred refinements and embodiments are the subject matter of the dependent claims.

This object is attained with the suggested method for automatically optimizing the calculation of an IOL to be implanted in which there are pre-surgical determination of at least the corneal topography, the eye length, the anterior chamber depth, calculation by means of ray tracing of the IOL to be implanted, and, post-cataract surgery, post-surgical determination of at least the corneal topography, the eye length, the anterior chamber depth, and the objective, wave front-based residual refraction, in that the pre-surgically and post-surgically determined measured values are used, in addition to automatic optimization of the surgically induced astigmatism and automatic optimization of the anatomical, post-surgical lens position for calculation of IOL to be implanted in the future.

The suggested method calculates an intraocular lens to be implanted. By taking the results of numerous cataract surgeries into account in the calculation of IOL to be implanted in the future, firstly, the calculation is automatically optimized, and secondly, the result that may be obtained from the cataract surgery is significantly enhanced.

DETAILED DESCRIPTION

The invention shall be described in greater detail in the following using exemplary embodiments.

The following occurs according to the method steps in the method for automatically optimizing the calculation of an IOL to be implanted:

a) pre-surgical determination of at least the corneal topography, the eye length, and the anterior chamber depth;
b) calculation by means of ray tracing of the IOL to be implanted; and,
C) after the cataract surgery has been performed, post-surgical determination of at least the corneal topography, eye length, anterior chamber depth, and objective, wave front-based residual refraction.

In accordance with the invention, the pre-surgically and post-surgically determined measured values are used in two additional method steps for calculating an IOL to be implanted in the future:

d) for automatically optimizing the surgically induced astigmatism, and,
e) for automatically optimizing the anatomical, post-surgical lens position.

In one embodiment of method step c), it is sufficient to perform a post-surgical determination of the corneal topography, the objective, wave front-based residual refraction, and either the eye length or the anterior chamber depth. This is sufficient because in this method step, (i.e., after a cataract surgery has been performed), the implanted IOL is known. Thus when the corneal topography and objective refraction are known, the eye length and anterior chamber depth may be calculated using the three known measured values. Since different devices are sometimes used for determining eye length and anterior chamber depth, this can simplify the measurement process.

The surgically induced astigmatism is automatically optimized in method step e) in that:
a number of corneal topographies that were measured pre-surgically are averaged and a number of corresponding corneal topographies that were measured post-surgically are averaged, and from these the difference of the mean deviation in pre-surgical and post-surgical corneal topography is calculated, and this mean deviation in corneal topography is included in the calculation model for the ray tracing for future calculation of an IOL to be implanted.

In contrast, the anatomical post-surgical lens position is optimized in method step f) in that:

an individual eye model is created using the post-surgical measured values, the IOL design used, and the post-surgical IOL position determined using prediction;

the post-surgical, wave front-based objective refraction is calculated;

the IOL position based on the prediction is modified in the individual eye model until the calculated objective refraction agrees with the measured objective refraction; and, the IOL position that is based on the prediction and that is determined in this manner may be taken into account for the future calculation of an IOL to be implanted.

It has proved particularly advantageous that during the modification of the IOL position in the individual eye model the same pupil size is used as during the measurement of the post-surgical wave front-based objective refraction.

While autorefractometers generally use only a subaperture of the actual pupil for the measurement, the wave front sensor uses the entire pupil, although only in a snapshot, so that this parameter may thus also be taken into account in the eye model.

Thus the anatomical lens position may be calculated very precisely, since both the refraction measured post-surgically (using the individual eye model) and the refraction measured pre-surgically by application of wave front sensor are based on an identical pupil size.

In accordance with the invention, the IOL position that is based on prediction is modified in the individual eye model such that the IOL position is displaced axially, tilted laterally, and/or rotated azimuthally. This ensures that the three correction values for the IOL—sphere, cylinder, and axis—are balanced.

The special advantage of the inventive method is that both the automatic optimization of the surgically induced astigmatism in accordance with method step d) and the automatic optimization of the anatomical, post-surgical lens position in accordance with method step e) may take place as a function of:

the IOL design used;
a defined patient group;
the doctor performing the cataract surgery;
the surgical technique used during the cataract surgery; and the like.

The listing herein is merely provided as an example, since in principle there are also other interrelationships and they may be taken into account. It is certain that the results of the cataract surgery are a function of the conditions listed herein. Thus for instance it is possible that both the post-surgical corneal topographies and also the post-surgical IOL position for the different IOL design are different. The same applies both for defined patient groups that may be classified by their ethnicity, age, sex, prior medical conditions, or the like, and for the technique used during the cataract surgery and the doctor performing it.

The use of the measured values determined pre-surgically and those determined post-surgically, taking into consideration the aforesaid interrelationships, also leads to both the automatic optimizing of the surgically induced astigmatism according to method step d) and the automatic optimizing of the anatomical post-surgical lens position according to method step e) attain an even more precise result.

The inventive solution makes available a method for calculating an intraocular lens to be implanted, with which method the calculation is automatically optimized in that the results of numerous cataract surgeries are taken into account during the calculation of intraocular lenses (IOL) to be implanted in the future.

The invention claimed is:

1. A method for automatically optimizing the calculation of an IOL to be implanted, comprising:
    a) determining pre-surgically at least corneal topography, eye length, and anterior chamber depth;
    b) calculating by application of ray tracing of the IOL to be implanted;
    c) post-surgically determining, after the cataract surgery has been performed, at least the corneal topography, the eye length, the anterior chamber depth, and an objective, wave front-based residual refraction;
    d) utilizing the pre-surgically and post-surgically determined measured values in two additional method steps:
    e) automatically optimizing the surgically induced astigmatism, and,
    f) automatically optimizing the anatomical, post-surgical lens position.

2. The method in accordance with claim 1, wherein for automatic optimization of the surgically induced astigmatism method step e) further comprises
    averaging a number of corneal topographies that were measured pre-surgically; and
    averaging a number of corresponding corneal topographies that were measured post-surgically;
    calculating a difference of mean deviation in pre-surgical and post-surgical corneal topography; and
    including the mean deviation in corneal topography in a calculation model for the ray tracing for future calculation of an IOL to be implanted.

3. The method in accordance with claim 2, wherein both the automatic optimization of the surgically induced astigmatism in accordance with method step d) and the automatic optimization of the anatomical post-surgical lens position in accordance with method step e) occur as a function of:
    an IOL design used;
    a defined patient group;
    a doctor performing the cataract surgery; and
    a surgical technique used during the cataract surgery.

4. The method in accordance with claim 1, wherein for automatic optimization of the anatomical, post-surgical lens position method step f) further comprises:
    creating an individual eye model using the post-surgical measured values, an IOL design used, and the post-surgical IOL position determined using prediction;
    calculating a post-surgical, wave front-based objective refraction;
    modifying the IOL position based on the prediction in the individual eye model until the calculated objective refraction agrees with the measured objective refraction; and,
    taking into account the IOL position that is based on the prediction and that is determined for the future calculation of an IOL to be implanted.

5. The method in accordance with claim 4, further comprising using a same pupil size during the modification of an IOL position in the individual eye model as is used during the measurement of the post-surgical wave front-based objective refraction.

6. The method in accordance claim 4, further comprising modifying the IOL position that is based on prediction in the individual eye model such that the IOL position is displaced axially, tilted laterally, and/or rotated azimuthally.

7. The method in accordance with claim 4, wherein both the automatic optimization of the surgically induced astigmatism in accordance with method step d) and the automatic optimization of the anatomical post-surgical lens position in accordance with method step e) occur as a function of:
- the IOL design used;
- a defined patient group;
- a doctor performing the cataract surgery;
- a surgical technique used during the cataract surgery.

8. The method in accordance claim 1, further comprising modifying an IOL position that is based on prediction in the individual eye model such that the IOL position is displaced axially, tilted laterally, and/or rotated azimuthally.

9. The method in accordance with claim 1, wherein both the automatic optimization of the surgically induced astigmatism in accordance with method step d) and the automatic optimization of the anatomical post-surgical lens position in accordance with method step e) occur as a function of:
- an IOL design used;
- a defined patient group;
- a doctor performing the cataract surgery; and
- a surgical technique used during the cataract surgery.

\* \* \* \* \*